United States Patent

Nardi et al.

[11] Patent Number: 5,922,917
[45] Date of Patent: Jul. 13, 1999

[54] PROCESS FOR THE PREPARATION OF 2-AMINO-1,3-PROPANEDIOL

[75] Inventors: Antonio Nardi, Paderno Dugnano; Marco Villa, Milan, both of Italy

[73] Assignee: Bracco International B.V., Amsterdam, Netherlands

[21] Appl. No.: 08/704,679

[22] PCT Filed: Apr. 5, 1995

[86] PCT No.: PCT/EP95/01245

§ 371 Date: Sep. 9, 1996

§ 102(e) Date: Sep. 9, 1996

[87] PCT Pub. No.: WO95/28379

PCT Pub. Date: Oct. 26, 1995

[30] Foreign Application Priority Data

Apr. 14, 1994 [IT] Italy .................................. MI94A0698

[51] Int. Cl.⁶ .................................................. C07C 213/02
[52] U.S. Cl. .......................................... 564/489; 564/507
[58] Field of Search ...................................... 564/489, 507

[56] References Cited

U.S. PATENT DOCUMENTS 3,737,462  6/1973  Cheema et al. ......................... 564/489
5,580,993  12/1996  Villa et al. .

FOREIGN PATENT DOCUMENTS

A 0238 961  9/1987  European Pat. Off. .

OTHER PUBLICATIONS

Piloty et al., Berichte der Deutschen Chemischen Gesellschaft, vol. 30, "Ueber Einige Aminoalkohole der Fettreihe", pp. 2057–2068, 1897.

Rylander, P., Catalytic Hydrogenation in Organic Synthesis, Academic Press, pp. 153–164, 1979.

Chemical Papers, vol. 43 (2)(1989),M.Fedoronko,et al., "Electroreduction of Triose Oximes" pp. 335–341 and p. 340.

Berichte der Deutschen Chemischen Gesellschaft, vol. 30 (1897) O.Piloty,et al.,"Ueber Einige Aminoalkohole Der Fettreihe" pp. 2057–2068 and p. 2061.

Primary Examiner—Peter O'Sullivan
Attorney, Agent, or Firm—Oblon, Spivak, McClelland, Maier & Neustadt, P.C.

[57] ABSTRACT

A process for the preparation of 2-amino-1,3-propanediol comprising the catalytic hydrogenation of 1,3-dihydroxyacetone oxime in the presence of rhodium supported on alumina is described.

10 Claims, No Drawings

PROCESS FOR THE PREPARATION OF 2-AMINO-1,3-PROPANEDIOL

The present invention relates to a process for the preparation of 2-amino-1,3-propanediol and, more particularly, it relates to a process for the preparation of 2-amino-1,3-propanediol starting from 1,3-dihydroxyacetone oxime.

2-Amino-1,3-propanediol, a compound better known as serinol, is a useful intermediate for the preparation of non-ionic iodinated contrast media (British patent No. 1472050 -Savac A. G.), in particular for the synthesis of Iopamidol (The Merck Index, XI Ed., page 799, No. 4943).

Several syntheses of serinol are known in the literature.

The U.S. Pat. No. 4,221,740 (Schering A. G.) and U.S. Pat. No. 4,448,999 (Dynamit Nobel A. G.), for instance, describe a process for the preparation of serinol through the reduction of the sodium salt of 2-nitro-1,3-propanediol.

U.S. Pat. No. 4,978,793 (W.R. Grace & Co.) describes a synthetic process comprising at first the preparation of ketals of 2-nitro-1,3-propanediol starting from nitromethane and formaldehyde and, subsequently, their reduction to the corresponding amino ketals which, in turn, can be hydrolyzed to serinol.

The patent application EP 0238961 (Merck Patent GmbH) describes a process for the preparation of serinol comprising the reduction of the corresponding ketimine which is obtained, in turn, by reacting 1,3-dihydroxyacetone with ammonia or with a primary amine.

It is also known in the literature, for instance as reported by Piloty et al. [Berichte, 30, (1897), 2057], that serinol can be prepared by reduction of 1,3-dihydroxyacetone oxime with sodium amalgam, in the presence of aluminum sulphate.

Alternatively, as described by M. Federonko [Chem. Papers, 43(2), 335–341, (1989)], serinol can be prepared by electrochemical reduction of 1,3-dihydroxyacetone oxime.

Said processes are of difficult industrial application and, with particular reference to the electrochemical reduction, remarkable quantities of by-products, variable depending on the selected operating conditions, were identified.

Catalytic hydrogenations of oximes in the presence of heterogeneous catalysts are also known in the literature as reported, for instance, by P. Rylander in "Catalytic Hydrogenation in Organic Syntheses", Academic Press, 1979, page 153–164.

Methods for the reduction of 1,3-dihydroxyacetone oxime by hydrogenation under heterogeneous catalysis, however, are not reported in the literature.

In this connection, we carried out hydrogenation reactions in the presence of conventional catalysts based on platinum or palladium. Independently from the selected operating conditions, the results were completely unsatisfactory affording, in the most favourable cases, the formation of serinol in traces.

We have instead surprisingly found that the catalytic hydrogenation reaction of 1,3-dihydroxyacetone oxime for the preparation of serinol can be easily carried out in the presence of a catalyst consisting of rhodium supported on alumina.

It is therefore the object of the present invention a process for the preparation of 2-amino-1,3-propanediol comprising the catalytic hydrogenation of 1,3-dihydroxyacetone oxime in a suitable solvent and in the presence of a catalyst consisting of rhodium supported on alumina.

The serinol thus prepared is a useful intermediate in the synthesis of Iopamidol, for instance, as described in the aforementioned British patent No. 1472050.

The process object of the present invention is of easy industrial application and 1,3-dihydroxyacetone oxime is a well-known compound, easily obtainable, according to conventional methods.

A convenient method for the preparation of 1,3-dihydroxyacetone oxime is described, for instance, in the literature by L. Reio [J. Chromatogr., 68, (1972), 183–205] and comprises the reaction between 1,3-dihydroxyacetone and hydroxylamine hydrochloride.

The reagents and the reaction products used in the process object of the present invention are stable and allow to operate on an industrial scale without using unusual technologies.

The reaction parameters of the process object of the present invention are reported and described as follows.

The hydrogenation reaction is carried out into a reactor suitable to sustain relatively high pressures, for instance into an autoclave, at a pressure preferably comprised between 40 and 70 bars ($4 \cdot 10^6$–$7 \cdot 10^6$ Pa).

The pressure does not seem to be a critical parameter.

At lower pressures, however, the kinetics of the reaction results to be rather slow, requiring thus particularly long times for the conversion of the oxime; higher pressures instead do not justify the relatively poor increase in the rate of the reaction.

The reaction temperature is comprised between 20° C. and 80° C.

Preferably, the operating temperature is comprised between 60° C. and 70° C.

At temperatures lower than 20° C. the reaction is rather slow while temperatures higher than 80° C. are useless.

The catalyst consists of rhodium supported on alumina at 5%, easily commercially available, and it is used in amounts comprised between 0.01 and 0.001 moles per mole of 1,3-dihydroxyacetone oxime.

Larger amounts of catalyst are equally effective but useless.

The hydrogenation reaction is carried out in the presence of suitable inert solvents.

With the term inert solvents we intend the solvents which do not undergo chemical reactions with the reagents or with the reaction products.

Suitable solvents are those commonly used in the catalytic hydrogenation reactions such as, for instance, lower $C_1$–$C_4$ alcohols. Methanol is preferably used.

In a preferred embodiment, the process object of the present invention is carried out according to the following operating conditions. A suitable amount of catalyst is added to a suitable amount of dihdroxyacetone oxime in a suitable solvent (for example methanol). The resultant system is put under hydrogen atmosphere, according to conventional techniques, at a pressure of about 70 bars ($7 \cdot 10^6$ Pa) and kept under stirring for a few hours (12–20) at the preselected temperature (for example 70° C.).

Due to the following practical features such as, for instance, the easy accessibility of the starting material, the stability of the reagents and of the products, the simple work-up of the reaction mixture and the easy industrial application, the present invention makes available a very advantageous process for the preparation of 2-amino-1,3-propanediol.

With the aim to better illustrate the present invention, without however limiting it, the following example is now given.

EXAMPLE 1

Preparation of 2-amino-1,3-propanediol 1,3-Dihydroxyacetone oxime (5 g; 47.6 mmoles), methanol (30 ml) and rhodium on alumina at 5% (0.1 g; 0.048 mmoles) were loaded into an autoclave-provided with mechanical stirring.

After removing the surrounding air, hydrogen at a pressure of 70 bars ($7 \cdot 10^6$ Pa) was loaded.

The resultant system was then kept under stirring at 70° C. for 16 hours.

At the end of the reaction, after emptying the reactor, the catalyst was filtered off on a celite bed and the solvent was evaporated at reduced pressure.

A crude product (4.5 g) was thus obtained.

From the crude, pure serinol was obtained by conversion into the corresponding hydrochloride according to the following method.

The reaction crude was treated with HCl 1 N up to nearly pH 1 and heated at 40° C. for 2 hours.

At the end, water was evaporated at reduced pressure and the resultant residue was collected with acetone (20 ml).

The mixture was kept under vigorous stirring for 3 hours.

Then, the precipitate was separated by filtration and dried at 50° C. and 25 mm/Hg.

Serinol hydrochloride (2.1 g) was thus isolated.

Alternatively, serinol can be purified by converting it into the corresponding oxalate, for instance, as described in the aforementioned patent application EP 0238961.

We claim:

1. A process for the preparation of 2-amino-1,3-propanediol comprising the catalytic hydrogenation of 1,3-dihydroxyacetone oxime in a suitable solvent and in the presence of a catalyst consisting of rhodium supported on alumina.

2. A process according to claim 1 wherein the catalytic hydrogenation is carried out at a pressure comprised between 40 and 70 bars.

3. A process according to claim 1 wherein the hydrogenation is carried out at a temperature comprised between 20° C. and 80° C.

4. A process according to claim 3 wherein the temperature is comprised between 60° C. and 70° C.

5. A process according to claim 1 wherein the catalyst consists of rhodium supported on alumina at 5%.

6. A process according to claim 1 wherein the catalyst is used in amounts comprised between 0.01 and 0.001 moles per mole of 1,3-dihydroxyacetone oxime.

7. A process according to claim 1 wherein the reaction solvent is a lower $C_1$–$C_4$ alcohol.

8. A process according to claim 6 wherein the solvent is methanol.

9. A process according to claim 1 comprising the catalytic hydrogenation of 1,3-dihydroxyacetone oxime at a pressure comprised between 40 and 70 bars and at a temperature comprised between 20° C. and 80° C., in a lower $C_1$–$C_4$ alcohol and in the presence of a catalyst consisting of rhodium supported on alumina at 5%, used in amounts comprised between 0.01 and 0.001 moles per mole of 1,3-dihydroxyacetone oxime.

10. A process for the preparation of 2-amino-1,3-propanediol which comprises the catalytic hydrogenation of 1,3-dihydroxyacetone oxime in a suitable solvent and in the presence of a catalyst consisting of rhodium supported on alumina at 5% in amounts of between 0.01 and 0.001 moles per mole of 1,3-dihydroxyacetone oxime.

* * * * *

UNITED STATES PATENT AND TRADEMARK OFFICE
CERTIFICATE OF CORRECTION

PATENT NO. : 5,922,917

DATED : July 13, 1999

INVENTOR(S): Antonio NARDI, et al.

It is certified that an error appears in the above-identified patent and that said Letters Patent is hereby corrected as shown below:

On the title page, item [86], § 371 and § 102(e) dates should be:

--Sep. 19, 1996--

Signed and Sealed this

Eleventh Day of July, 2000

Attest:

Q. TODD DICKINSON

*Attesting Officer*     *Director of Patents and Trademarks*